United States Patent [19]

Salzburg et al.

[11] Patent Number: 4,666,930
[45] Date of Patent: May 19, 1987

[54] 3-HYDRAZONO-BENZISOTHIAZOLE 1,1-DIOXIDE FUNGICIDES

[75] Inventors: Herbert Salzburg; Manfred Hajek, both of Cologne; Gerd Hänssler, Leverkusen, all of Fed. Rep. of Germany

[73] Assignee: Bayer Aktiengesellschaft, Leverkusen, Fed. Rep. of Germany

[21] Appl. No.: 707,361

[22] Filed: Mar. 1, 1985

[30] Foreign Application Priority Data

Mar. 8, 1984 [DE] Fed. Rep. of Germany ....... 3408540

[51] Int. Cl.$^4$ .................. C07D 275/06; A01N 43/80
[52] U.S. Cl. .................................... 514/373; 548/207
[58] Field of Search ............... 548/207, 209, 210, 212; 514/373

[56] References Cited

U.S. PATENT DOCUMENTS

| | | | |
|---|---|---|---|
| 3,225,056 | 12/1965 | Traverso et al. | 548/212 |
| 3,790,587 | 2/1974 | Boshagen et al. | 548/212 |
| 4,108,860 | 8/1978 | Wade et al. | 548/212 |
| 4,140,693 | 2/1979 | Wade et al. | 548/212 |
| 4,174,442 | 11/1979 | Wade et al. | 548/207 |
| 4,177,191 | 12/1979 | Wade et al. | 548/212 |
| 4,178,451 | 12/1979 | Wade et al. | 546/272 |
| 4,379,157 | 4/1983 | van Hes et al. | 514/373 |

FOREIGN PATENT DOCUMENTS

| | | | |
|---|---|---|---|
| 0086748 | 8/1983 | European Pat. Off. | |
| 154273 | 9/1985 | European Pat. Off. | 514/373 |
| 3343091 | 6/1985 | Fed. Rep. of Germany | 514/373 |
| 48-24735 | 7/1973 | Japan | 548/210 |
| 6020580 | 2/1981 | Japan | 514/373 |

OTHER PUBLICATIONS

Whitehead et al, "Hypotensive 1,2-Benzisothiazole 1,1-Dioxides II", J. Med. Chem., 10, pp. 844–849 (1967).
Chem. Abstract, 73:45 500, (Jap. 7,014,301).
J. Am. Chem. Soc., 65, "Pseudo-saccharin Chloride . . . ", pp. 457–458 (1943).

Primary Examiner—Robert Gerstl
Assistant Examiner—G. Hendricks
Attorney, Agent, or Firm—Sprung Horn Kramer & Woods

[57] ABSTRACT

Compounds of the formula

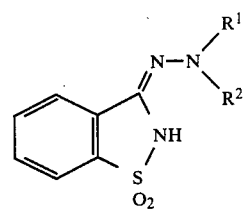

in which
R$^1$ is alkyl, cycloalkyl, aryl or hydrogen,
R$^2$ is —CO—R$^3$,
R$^3$ is alkyl, alkenyl or cycloalkyl, or is phenyl which is optionally substituted, or is alkoxy or benzyl, or is phenoxy which is optionally substituted, or is phenoxymethyl, alkylamino, cycloalkylamino or phenylamino, or
R$^1$ and R$^2$ together are a

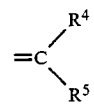

group,
R$^4$ and R$^5$ each independently is hydrogen, alkyl, cycloalkenyl or phenylalkenyl, or is phenyl which is optionally substituted by alkyl, halogen and/or alkoxy, or is furyl, or
R$^4$ and R$^5$ together are alkylene having 4 to 6 carbon atoms,
are fungicidally active. Those compounds wherein R$^3$ is alkylamino, cycloalkylamino or phenylamino, with the exception of the compound in which R$^1$ is hydrogen and R$^6$ is phenylamino, are new.

5 Claims, No Drawings

3-HYDRAZONO-BENZISOTHIAZOLE 1,1-DIOXIDE FUNGICIDES

The present invention relates to the use of 3-hydrazino-1,2-benzisothiazole 1,1-dioxide derivatives as fungicides, the majority of these derivatives being known. The use of the 3-hydrazino-1,2-benzisothiazole 1,1-dioxide derivatives in pharmacology is known (see Whitehead et al, J. Med. Chem. 10, 844 et seq., (1967)). Their use in the field of plant protection, especially as fungicides, is new.

3-Alkenyloxy-1,2-benzisothiazole 1,1-dioxides, for example 3-allyloxy-1,2-benzisothiazole 1,1-dioxide, are also known, as is their action in the field of plant protection (see Japanese Patent No. 7,014,301; and CA 73: 45,500 m).

It has been found that the 3-hydrazino-1,2-benzisothiazole 1,1-dioxide derivatives which are known medicaments and are of the general formula (I)

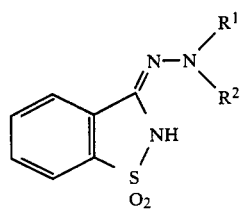

in which
$R^1$ represents alkyl, cycloalkyl, aryl or hydrogen,
$R^2$ represents —CO—$R^3$,
wherein
$R^3$ represents alkyl, alkenyl or cycloalkyl, or represents phenyl which is optionally monosubstituted to pentasubstituted by identical or different substituents, or represents alkoxy or benzyl, or represents phenoxy which is optionally monosubstituted to pentasubstituted by identical or different substituents, or represents phenoxymethyl, alkylamino, cycloalkylamino or phenylamino, or
$R^1$ and $R^2$ together represent a

group,
wherein
$R^4$ and $R^5$ are identical or different and represent hydrogen, alkyl, alkenyl, cycloalkenyl or phenylalkenyl, or represent phenyl which is optionally monosubstituted to pentasubstituted by identical or different substituents from amongst alkyl, halogen and alkoxy, or represent furyl, or
$R^4$ and $R^5$ represent alkylene having 4 to 6 carbon atoms,
possess good fungicidal properties.

Surprisingly, the 3-hydrazino-1,2-benzisothiazole 1,1-dioxide derivatives of the formula (I) have a greater fungicidal action, in particular a systemic action, than the compounds which are known from the prior art and have the same direction of action. The novel use, according to the invention, of the 3-hydrazino-1,2-benzisothiazole 1,1-dioxide derivatives thus represents an enrichment of the art.

Formula (I) gives a general definition of the 3-hydrazino-1,2-benzisothiazole 1,1-dioxide derivatives to be used according to the invention.

The compounds of the formula (I) are in general in equilibrium with the compounds of the formula (IA):

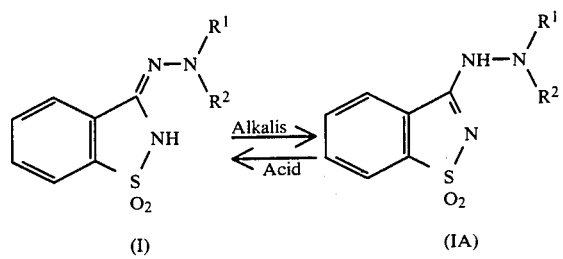

For the sake of simplicity, reference will always be made below to compounds of the formula (I), although the pure compounds or their mixtures with various amounts of the compounds of formulae (I) and (IA) are meant.

Preferred compounds of the formula (I) are those in which
$R^1$ represents hydrogen, alkyl having 1 to 4 carbon atoms, cycloalkyl having 5 or 6 carbon atoms or phenyl,
$R^2$ represents —CO—$R^3$,
wherein
$R^3$ represents alkyl having 1 to 4 carbon atoms, cyclohexyl, benzyl, phenyl, alkoxy having 1 to 4 carbon atoms of phenoxymethyl, or represents phenoxy which is optionally monosubstituted to trisubstituted by halogen, or represents alkylamino having 1 to 4 carbon atoms, cycloalkylamino having 5 or 6 carbon atoms or phenylamino, or
$R^1$ and $R^2$ together represent a

group,
wherein
$R^4$ represents hydrogen or alkyl having 1 to 3 carbon atoms,
$R^5$ represents alkyl having 1 to 4 carbon atoms, alkenyl having 2 to 5 carbon atoms, cycloalkenyl having 5 or 6 carbon atoms, phenylvinyl or furyl, or represents phenyl which is optionally monosubstituted to trisubstituted by halogen, in particular fluorine and chlorine, alkyl having 1 to 3 carbon atoms and alkoxy having 1 to 3 carbon atoms, or
$R^4$ and $R^5$ represents alkylene having 4 or 5 carbon atoms.

Particularly preferred compounds of the formula (I) are those
in which
$R^1$ represents hydrogen or methyl,
$R^2$ represents —CO—$R^3$,
wherein
$R^3$ represents methyl, ethyl, n- and iso-propyl, phenyl, benzyl, phenoxymethyl, methoxy, ethoxy and n- and iso-propoxy, or represents phenoxy which is optionally monosubstituted or disubstituted by chlorine, or represents methylamino, ethylamino, n- and isopropylamino, cyclohexylamino or phenylamino, or $R^1$ and $R^2$ together represent a

group,
wherein $R^4$ represents hydrogen, methyl or ethyl, $R^5$ represents methyl, ethyl, n- and iso-propyl, ethenyl, 1-methyl-ethenyl, allyl, propenyl, 1-methyl-propenyl, cyclohexenyl, phenylvinyl or furyl, or represents phenyl which is optionally monosubsituted or disubstituted by fluorine, chlorine, methyl, ethyl, methoxy and ethoxy, or $R^4$ and $R^5$ represent tetramethylene or pentamethylene.

The majority of the 3-hydrazino-1,2-benzisothiazole 1,1-dioxide derivatives of the formula (I) which are to be used according to the invention are known. They can be prepared by known processes (see, for example, Whitehead et al, J. Med. Chem. 10, 844-849 (1967) or J. Am. Chem. Soc. 65, 457-458 (1943)). Thus, 3-hydrazino-2H,3H-1,2-benzisothiazole 1,1-dioxide can be reacted with activated carboxylic acid derivatives, such as anhydrides and halides, according to the following equation:

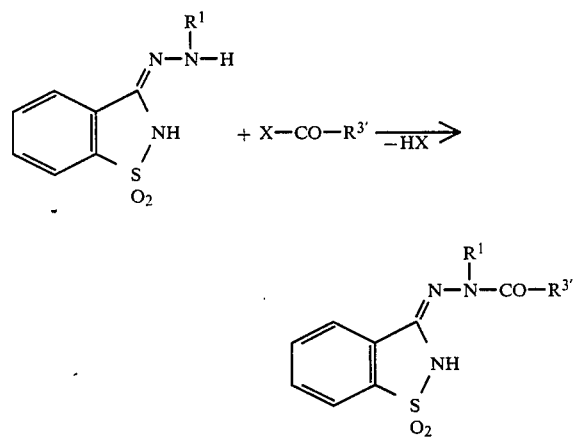

wherein $R^1$ has the meaning given above, $R^{3'}$ has the meaning given above for $R^3$, with the exception of the amide derivatives, and X represents halogen or the —O—CO—$R^{3'}$ radical.

The reaction is usually carried out under atmospheric pressure and at a temperature of 0° C. to 100° C., if appropriate in the presence of an auxiliary base for the reaction with halides, and in the presence of inert solvents, such as, for example, dioxane, chloroform, methylene chlorides or toluene, by the standard methods of organic chemistry.

The compounds of the formula (I), in which $R^1$ and $R^2$ together represent a

group, can also be prepared by known processes (see Whitehead et al, J. Med. Chem. 10, 844-849 (1967)). 3-Hydrazino-1,2-benzisothiazole 1,1-dioxide is reacted with oxo compounds by the following equation:

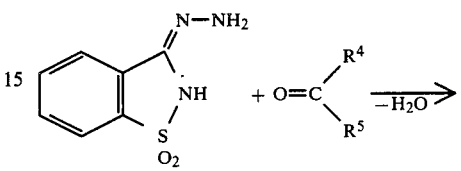

wherein $R^4$ and $R^5$ have the meaning given above.

In general, the reactants are reacted in stoichiometric amounts, in a suitable solvent, while heating. Examples of suitable solvents are dioxane, ethanol, dimethylformamide and toluene.

The process is normally carried out under atmospheric pressure, the temperature being between 10° C. and 120° C., as a rule 80°-100° C.

Preferred oxo compounds according to the invention are aldehydes, such as, for example, acetaldehyde, butyraldehyde and isobutyraldehyde, benzaldehyde, 3-chlorobenzaldehyde, 3,4-dichlorobenzaldehyde, 4-chlorobenzaldehyde, 4-methoxybenzaldehyde, 3- and 4-fluorobenzaldehyde, acrolein, methacrolein, 2-furylaldehyde, 2-methylpropenylaldehyde, $\Delta^3$-cyclohexenylaldehyde, indolylaldehyde and styrylaldehyde.

Examples of preferred ketones are acetone, cyclopentanone, cyclopentenone, cyclohexanone and methyl ethyl ketone.

The compounds of the formula (IB)

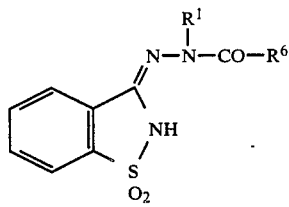

in which $R^1$ has the meaning given in formula (I) and $R^6$ represents alkylamino, cycloalkylamino or phenylamino, with the exception of the compound in which $R^1$ represents hydrogen and $R^6$ represents phenylamino (see Whitehead, J. Med. Chem. 10, 844 et seq. (1967)), are new; however, they can be prepared by well known methods of classical organic chemistry by, for example, reacting 3-hydrazino-2H,3H-1,2-benzisothiazole 1,1-dioxides of the formula (II)

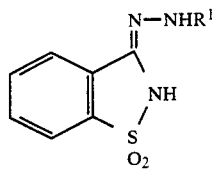
(II)

in which
R¹ has the meaning given above,
with isocyanates of the formula (III)

$$OCNR^6 \qquad (III)$$

in which
R⁶ has the meaning given above, if appropriate in the presence of an inert solvent, as already stated above, preferably under atmospheric pressure, in general in an equimolar ratio.

The active compounds which can be used according to the invention exhibit a powerful microbicidal action and can be employed in practice for combating undesired micro-organisms. The active compounds are suitable for use as plant protection agents, especially as fungicides; some compounds also possess bactericidal activity.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and selective herbicides, and as mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, forming, painting, etc. It is also possible to apply the active compounds by the ultra low volume method, or to inject the formulations of the active compound or the active compound itself into the soil. It is also possible to treat the seed of the plants.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

USE EXAMPLES

The compound shown below is used as a comparative substance in the test examples.

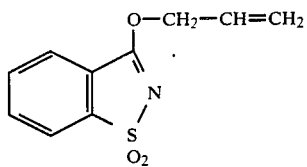

greenhouse at 100% relative atmospheric humidity and 25° C.

Evaluation of the disease infestation is carried out 4 days after the inoculation.

In this test, a superior activity compared with the prior art is shown, for example, by the compounds according to the following examples:

TABLE A

Pyricularia Test (Rice)/protective

| Active compounds | Active compound concentration in % | Disease infestation as a percentage of the untreated control |
|---|---|---|
| [structure: O—CH₂—CH=CH₂ benzisothiazole S,S-dioxide] (known) | 0.025 | 25 |
| [structure: N—N(H)—C(=O)—N(H)—CH(CH₃)₂ with benzene-NH-SO₂] | 0.025 | 10 |
| [structure: N—NH—C(=O)—NH—cyclohexyl with benzene-NH-SO₂] | 0.025 | 30 |
| [structure: N—N=CH—CH(CH₃)₂ with benzene-NH-SO₂] | 0.025 | 20 |
| [structure: N—N(H)—C(=O)—CH₃ with benzene-NH-SO₂] | 0.025 | 20 |

EXAMPLE A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a

EXAMPLE B

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C.

and a relative atmospheric humidity of 100% until they are evaluated.

Evaluation of the disease infestation is carried out 4 days after the inoculation.

In this test, a superior activity compared with the prior art is shown, for example, by the compounds according to the following examples:

TABLE B

Pyricularia Test (Rice)/systemic

| Active compounds | Amount applied, in mg of active compound per 100 cm² | Disease infestation as a percentage of the untreated control |
|---|---|---|
| benzisothiazole-O-CH₂-CH=CH₂ (known) | 100 | 50 |
| N-NH-C(=O)-NH-CH(CH₃)₂ hydrazide sulfonamide | 100 | 22 |
| N-NH-C(=O)-NH-cyclohexyl | 100 | 20 |
| N-NH-C(=O)-NH-CH₃ | 100 | 10 |
| N-NH-C(=O)-NH-C₆H₅ | 100 | 20 |
| N-N=CH-CH(CH₃)₂ | 100 | 33 |
| N-NH-C(=O)-CH₃ | 100 | 11 |
| N-NH-C(=O)-C₆H₅ | 100 | 22 |

PREPARATION EXAMPLES

The following examples are intended to illustrate the invention without restricting it:

EXAMPLE 1

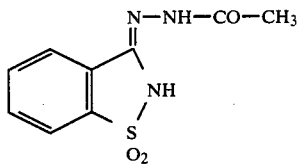

9.8 g (0.05 mol) of 3-hydrazino-2H,3H-1,2-benzisothiazole 1,1-dioxide in an excess (15 g) of acetic anhydride are brought to 60° C., the temperature being increased slowly. After 2 hours, the mixture is cooled and evaporated down, and the residue is recrystallized from ethanol. 9.4 g (79% of theory) of 3-acetylhydrazino-1,2-benzisothiazole 1,1-dioxide of melting point 274° C. are obtained.

EXAMPLE 2

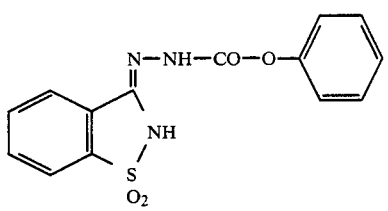

5 g (0.05 mol) of triethylamine are added to 9.8 g (0.05 mol) of 3-hydrazino-2H,3H-1,2-benzisothiazole 1,1-dioxide in 100 ml of dioxane, and 8.6 g (0.55 mol) of phenoxycarbonyl chloride, dissolved in 25 ml of dioxane, are then added dropwise to the stirred mixture. After about 2 hours, the precipitated salt is filtered off under suction and washed with 15 ml of cold dioxane, and the combined mother liquors are evaporated down. Crystallization from ethanol gives 12.8 g (81% of theory) of 3-phenoxycarbonylhydrazino-2H,3H-1,2-benzisothiazole 1,1-dioxide of melting point 216° C.

EXAMPLE 3

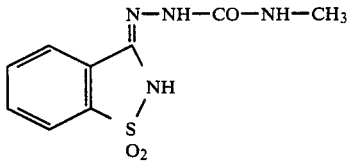

A solution of 3.7 g (0.55 mol) of methyl isocyanate in 30 ml of dioxane is added dropwise to 9.8 g (0.05 mol) of 3-hydrazino-2H,3H-1,2-benzisothiazole 1,1-dioxide in 100 ml of dioxane at room temperature. Stirring is continued for 1 hour, after which the product is filtered off under suction. 11.8 g (89% of theory) of 3-methylaminocarbonylhydrazino-1,2-benzisothiazole 1,1-dioxide of melting point 183° C. are obtained. The product can be recrystallized from ethanol.

The following compounds of the formula

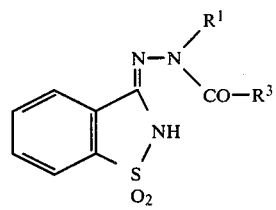

can be prepared analogously to Examples 1 to 3:

| Example No. | R$^1$ | R$^3$ | Melting point (°C.) |
|---|---|---|---|
| 4 | H | —CH$_3$ | 274 |
| 5 | CH$_3$ | —CH$_3$ | 193 |
| 6 | H | —C$_2$H$_5$ | 211 |
| 7 | CH$_3$ | —C$_2$H$_5$ | 189 |
| 8 | H | —C$_3$H$_7$—n | 110 |
| 9 | H | —C$_6$H$_5$ | 272 |
| 10 | H | —CH$_2$—C$_6$H$_5$ | 232 |
| 11 | H | —CH$_2$—O—C$_6$H$_5$ | 239 |
| 12 | H | —O—CH$_3$ | 211 |
| 13 | H | —O—C$_2$H$_5$ | 207 |
| 14 | CH$_3$ | —O—C$_2$H$_5$ | 191 |
| 15 | H | OC$_6$H$_5$ | 216 |
| 16 | H | —O—C$_6$H$_4$—Cl | 227 |
| 17 | H | —NH—CH$_3$ | 183 |
| 18 | H | —NH—C$_3$H$_7$—iso | 240 |
| 19 | H | —NH—C$_6$H$_{11}$ | 220 |
| 20 | H | —NH—C$_6$H$_5$ | 208 |

EXAMPLE 21

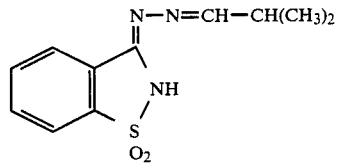

19.7 g (0.1 mol) of 3-hydrazino-2H,3H-1,2-benzisothiazole 1,1-dioxide are dissolved in 200 ml of dioxane at 40°-50° C., and 8 g (0.11 mol) of isobutyraldehyde are added dropwise to the thoroughly stirred mixture. The product is precipitated directly during this procedure. When the addition is complete, the mixture is heated to 80°-90° C. for about 20 minutes and then cooled, and the crystals are filtered off under suction. 22.1 g (88.1% of theory) of 3-isobutylidenehydrazino-1,2-benzisothiazole 1,1-dioxide of melting point 225° C. are obtained in this manner.

EXAMPLE 22

24.3 g (81% of theory) of 3-[4-methylbenzylidenehydrazino]-1,2-benzisothiazole, 1,1-dioxide of melting point 294° C. are obtained analogously to Example 21, in a 0.1 molar batch, using 13.2 g (0.11 mol) of 4-methylbenzaldehyde.

EXAMPLE 23

15.2 g (61% of theory) of 3-(2-methylallylidenehydrazino)-1,2-benzisothiazole 1,1-dioxide of melting point 224° C. are obtained analogously to Example 21, using 0.2 mol of methacrolein in a 0.1 molar batch.

The following compounds of the formula

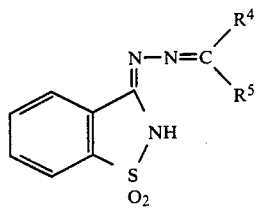

can be prepared analogously to Examples 21 to 23:

| Example No. | R⁴ | R⁵ | Melting point (°C.) |
| --- | --- | --- | --- |
| 24 | H | CH₂=C(CH₃)— | 224 |
| 25 | H | CH₃CH=CH— | 196 |
| 26 | H | 2-Furyl- | 257 |
| 27 | H | CH₃CH=C(CH₃)— | 262 |
| 28 | H | Δ³-cyclohexenyl | 221 |
| 29 | H | C₆H₅CH=CH— | 260 |
| 30 | H | —CH(CH₃)₂ | 225 |
| 31 | CH₃ | CH₃ | 215 |
| 32 | | cyclopentylidene | 231 |
| 33 | | cyclohexylidene | 177 |
| 34 | H | 3,4-Cl₂—C₆H₃— | 321 |
| 35 | H | 3-Cl—C₆H₄— | 306 |
| 36 | H | 4-Cl—C₆H₄ | 315 |
| 37 | H | 3-CH₃O—C₆H₄— | 264 |
| 38 | H | 4-CH₃O—C₆H₄— | 281 |
| 39 | H | 4-F—C₆H₄— | 302 |
| 40 | H | 3-F—C₆H₄— | 318 |
| 41 | H | 4-CH₃—C₆H₄— | 294 |
| 42 | H | C₆H₅— | 287 |

It is understood that the specification and examples are illustrative but not limitative of the present invention and that other embodiments within the spirit and scope of the invention will suggest themselves to those skilled in the art.

We claim:

1. A method of combating fungi which comprises applying to such fungi or to a fungus habitat a fungicidally effective amount of a 3-hydrazino-1,2-benziosothiazole 1,1-dioxide derivative of the formula

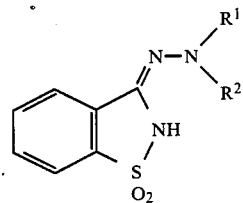

in which
$R^1$ is alkyl having 1 to 4 carbon atoms, cycloalkyl having 5 or 6 carbon atoms, phenyl or hydrogen,
$R^2$ is —CO—$R^3$,
$R^3$ is lower alkyl, alkoxy having 1 to 4 carbon atoms or alkenyl having 2 to 4 carbon atoms or cyclohexyl, or is phenyl, or is benzyl, or is phenoxy which is optionally halogen substituted, or is phenoxymethyl, alkylamino having 1 to 4 carbon atoms, cycloalkylamino having 5 or 6 carbon atoms or phenylamino, or
$R^1$ and $R^2$ together are a

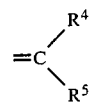

group,
$R^4$ and $R^5$ each independently is hydrogen, alkyl having 1 to 4 carbon atoms, alkenyl having 2 to 5 carbon atoms, cycloalkenyl having 5 or 6 carbon atoms or phenylvinyl, or is phenyl which is optionally substituted by alkyl having 1 to 3 carbon atoms, halogen and/or alkoxy having 1 to 3 carbon atoms, or is furyl, or
$R^4$ and $R^5$ together are alkylene having 4 to 6 carbon atoms.

2. The method according to claim 1, in which
$R^1$ is hydrogen, alkyl having 1 to 4 carbon atoms, cycloalkyl having 5 or 6 carbon atoms or phenyl,
$R^2$ is —CO—$R^3$,
$R^3$ is alkyl having 1 to 4 carbon atoms, cyclohexyl, benzyl, phenyl, alkoxy having 1 to 4 carbon atoms, or phenoxymethyl, or is phenoxy which is optionally monosubstituted to trisubstituted by halogen, or is alkylamino having 1 to 4 carbon atoms, cycloalkylamino having 5 or 6 carbon atoms or phenylamino, or
$R^1$ and $R^2$ together are a

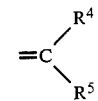

group,
$R^4$ is hydrogen or alkyl having 1 to 3 carbon atoms,
$R^5$ is alkyl having 1 to 4 carbon atoms, alkenyl having 2 to 5 carbon atoms, cycloalkenyl having 5 or 6 carbon atoms, phenylvinyl or furyl, or is phenyl which is optionally monosubstituted to trisubstituted by halogen, alkyl having 1 to 3 carbon atoms and/or alkoxy having 1 to 3 carbon atoms, or
$R^4$ and $R^5$ together are alkylene having 4 or 5 carbon atoms.

3. The method according to claim 1, in which
$R^1$ is hydrogen or methyl,
$R^2$ is —CO—$R^3$,
$R^3$ is methyl, ethyl, n- and iso-propyl, phenyl, benzyl, phenoxymethyl, methoxy, ethoxy and n- and iso-propoxy, or is phenoxy which is optionally monosubstituted or disubstituted by chlorine, or is methylamino, ethylamino, n- or iso-propylamino, cyclohexylamino or phenylamino, or
$R^1$ and $R^2$ together are a

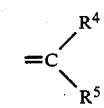

group,
$R^4$ is hydrogen, methyl or ethyl,
$R^5$ is methyl, ethyl, n- or iso-propyl, ethenyl, 1-methyl-ethenyl, allyl, propenyl, 1-methylpropenyl, Δ³-cyclohexenyl, phenylvinyl or furyl, or is phenyl which is optionally monosubstituted or disubstituted by fluorine, chlorine, methyl, ethyl, methoxy and/or ethoxy, or $R^4$ and $R^5$ together are tetramethylene or pentamethylene.

4. The method according to claim 1, in which
$R^1$ is hydrogen,
$R^2$ is $-CO-R^3$,
$R^3$ is alkyl having 1 to 4 carbon atoms, cyclohexyl, benzyl, phenyl, or phenoxymethyl, or is alkylamino having 1 to 4 carbon atoms, cycloalkylamino having 5 or 6 carbon atoms or phenylamino, or
$R^1$ and $R^2$ together are a

group,
$R^4$ is hydrogen or alkyl having 1 to 3 carbon atoms,
$R^5$ is alkyl having 1 to 4 carbon atoms, or is phenyl which is optionally monosubstituted to trisubstituted by halogen, alkyl having 1 to 3 carbon atoms and/or alkoxy having 1 to 3 carbon atoms, or
$R^4$ and $R^5$ together are alkylene having 4 or 5 carbon atoms.

5. The method according to claim 1, wherein such compound is
3-methylaminocarbonylhydrazino-1,2-benzisothiazole 1,1-dioxide,
3-isopropylaminocarbonylhydrazino-1,2-benzisothiazole 1,1-dioxide,
3-cyclohexylaminocarbonylhydrazino-1,2-benzisothiazole 1,1-dioxide,
3-phenylaminocarbonylhydrazino-1,2-benziosothiazole 1,1-dioxide or
3-isobutylidenehydrazino-1,2-benziosothiazole 1,1-dioxide.

* * * * *